US005693502A

United States Patent [19]
Gold et al.

[11] Patent Number: 5,693,502
[45] Date of Patent: Dec. 2, 1997

[54] NUCLEIC ACID LIGAND INHIBITORS TO DNA POLYMERASES

[75] Inventors: Larry Gold; Sumedha D. Jayasena, both of Boulder, Colo.

[73] Assignee: NeXstar Pharmaceuticals, Inc., Boulder, Colo.

[21] Appl. No.: 484,557

[22] Filed: Jun. 7, 1995

Related U.S. Application Data

[63] Continuation-in-part of Ser. No. 964,624, Oct. 21, 1992, Pat. No. 5,496,938, and Ser. No. 714,131, Jun. 10, 1991, Pat. No. 5,475,096, which is a continuation-in-part of Ser. No. 536,428, Jun. 11, 1990, abandoned.

[51] Int. Cl.$^6$ ................................................. C12P 19/34
[52] U.S. Cl. ........................................ 435/91.2; 435/810
[58] Field of Search ............................ 435/91.2, 6, 810

[56] References Cited

U.S. PATENT DOCUMENTS

| | | | |
|---|---|---|---|
| 5,270,163 | 12/1993 | Gold et al. | 435/6 |
| 5,338,671 | 8/1994 | Scalice et al. | 435/91.2 |
| 5,459,015 | 10/1995 | Janjic et al. | 435/6 |
| 5,472,841 | 12/1995 | Jayasena et al. | 435/6 |
| 5,476,766 | 12/1995 | Gold et al. | 435/6 |
| 5,496,938 | 3/1996 | Gold et al. | 536/22.1 |
| 5,503,978 | 4/1996 | Schneider et al. | 435/6 |
| 5,527,894 | 6/1996 | Gold et al. | 536/22.1 |
| 5,543,293 | 8/1996 | Gold et al. | 435/6 |
| 5,567,588 | 10/1996 | Gold et al. | 435/6 |
| 5,580,737 | 12/1996 | Polisky et al. | 435/6 |
| 5,587,468 | 12/1996 | Allen et al. | 536/22.1 |
| 5,595,877 | 1/1997 | Gold et al. | 435/6 |

FOREIGN PATENT DOCUMENTS

| | | | |
|---|---|---|---|
| 2 183 661 | 6/1987 | United Kingdom . | |
| WO 89/06694 | 7/1989 | WIPO . | |
| WO92/14843 | 9/1992 | WIPO | C12Q 1/68 |
| WO94/25037 | 11/1994 | WIPO | A61K 31/70 |

OTHER PUBLICATIONS

Tuerk et al. (1992) Proc. Natl. Acad. Sci. USA 89:6988–92.
Chen and Gold (1994) Biochemistry 33:8746–56.
Fujihashi et al. (1995) AIDS Research and Human Retroviruses 11:461–471.
Tökés and Aradi (1995) Biochimica et Biophysica Acta 1261:115–120.
Hacia et al. (1994) Biochemistry 33:6192–6200.
Boiziau et al. (1995) Nucl. Acids Res. 23:64–71.
Matsukura et al. (1995) Toxicology Letters 82/83:435–38.
Takase–Yoden et al. (1995) Antiviral Res. 28:359–68.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Bloch (1992) Amplications, a Forum for PCR Users, Issue 8, pp. 6–9.
(1992) Amplications, A Forum for PCR Users, Issue 8 pp. 16–17.
Myers and Gelfand (1991) Biochemistry 30:7661.
Kellogg et al. (1994) BioTechniques 16:1134.
Tamura et al. (1995) Nucleic Acids Research 34:93–94.

*Primary Examiner*—Stephanie W. Zitomer
*Assistant Examiner*—Amy Atzel, Ph.D.
*Attorney, Agent, or Firm*—Swanson & Bratschun LLC

[57] ABSTRACT

This invention discloses high-affinity oligonucleotide ligands to the thermostable Taq polymerase and Tth polymerase. Specifically, this invention discloses DNA ligands having the ability to bind to the Taq and Tth polymerases and the methods for obtaining such ligands. The ligands are capable of inhibiting polymerases at ambient temperatures.

3 Claims, 8 Drawing Sheets

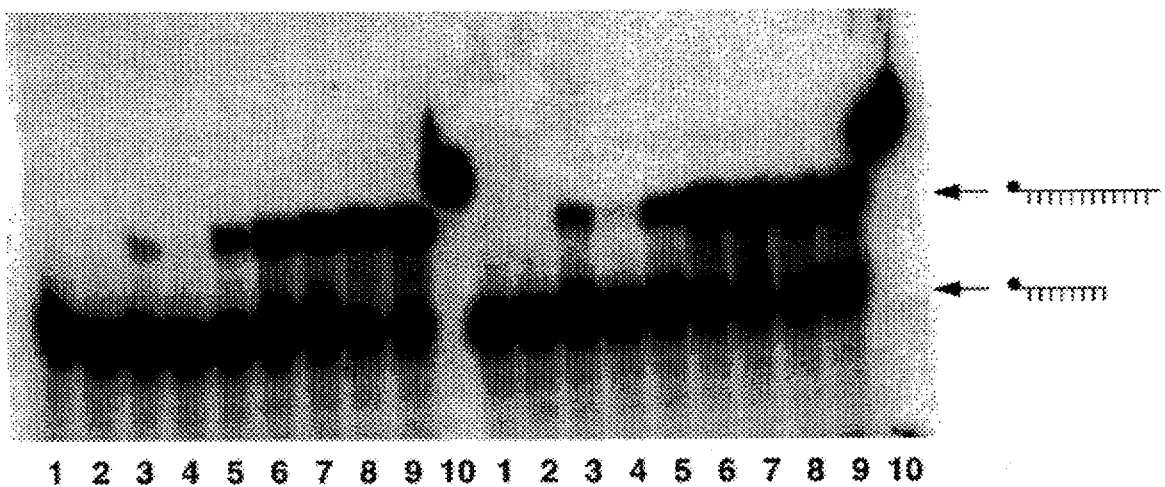

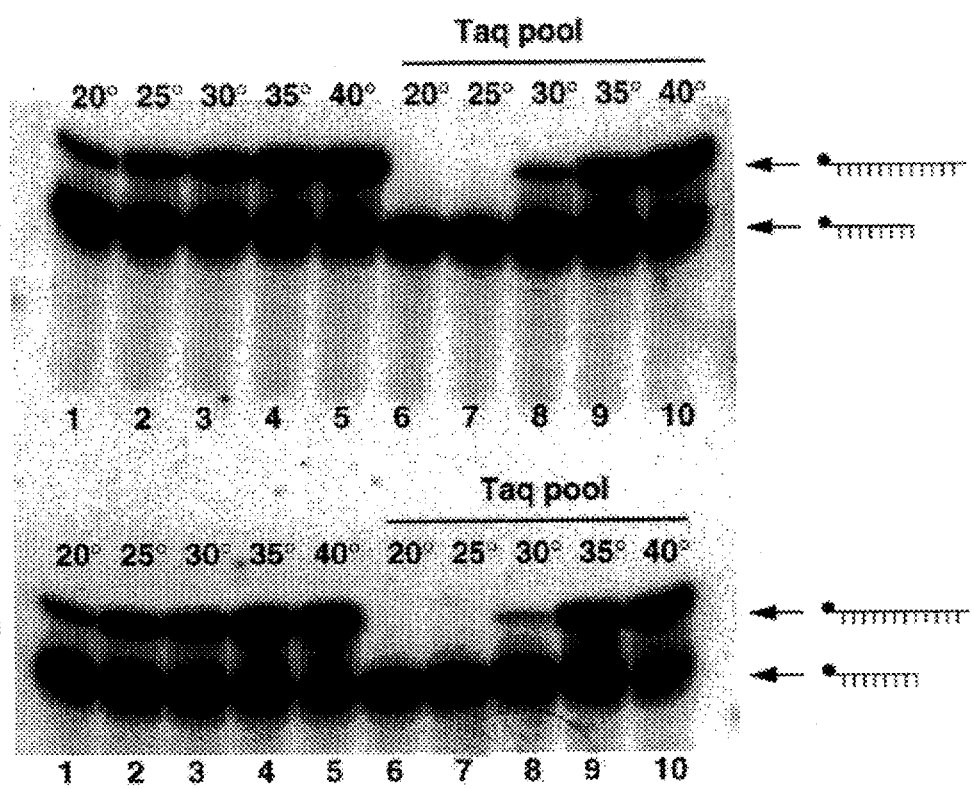

SEQUENCE LISTING ( 1 ) GENERAL INFORMATION:

( i i i ) NUMBER OF SEQUENCES: 74

( 2 ) INFORMATION FOR SEQ ID NO:1:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:

( x i ) SEQUENCE DESCRIPTION: SEQ ID NO:1:

TTCTCGGTTG GTCTCTGGCG GAGCNNNNNN NNNNNNNNNN NNNNNNNNNN    50

NNNNTCTTGT GTATGATTCG CTTTTCCC 78

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

TTCTCGGTTG GTCTCTGGCG GAGC 24

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TAGGGAAAAG CGAATCATAC ACAAGA 26

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:4:

GGCGAATTCT TCTCGGTTGG TCTCTGGCGG AGC 33

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CGCGGATCCT AATACGACTC ACTATAGGGA AAAGCGAATC ATACACAAGA 50

(2) INFORMATION FOR SEQ ID NO:6:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATGCCTAAGT TCGAACGCG GCTAGCCAGC TTTGCTGGC TAGCCGCGT 49

(2) INFORMATION FOR SEQ ID NO:7:

(i) SEQUENCE CHARACTERISTICS:
        (A) LENGTH: 26 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

TATCGTTTAC TCATTGTTTT GTGTGT      26

( 2 ) INFORMATION FOR SEQ ID NO:8:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:8:

ACATTACCCG AGACATTCCT GACGTTTTG      29

( 2 ) INFORMATION FOR SEQ ID NO:9:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:9:

TGCTGCTCCT TGTTCGTTTT GTCT      24

( 2 ) INFORMATION FOR SEQ ID NO:10:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

AGCTTTTGGG GACATTCTAA CGTTTTGTCA      30

( 2 ) INFORMATION FOR SEQ ID NO:11:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:11:

AGATGCTTCA GTTTTCTCTC CGTG      24

( 2 ) INFORMATION FOR SEQ ID NO:12:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:12:

TCTTTTGGAC TGAAGGTTTG TTGGT         25

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ATGGTCTTTT TGTTGTTTGT TTG         23

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

GTGACTTTTT ACTTGTCCTA GGCTG         25

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CATCTATGTC TTCTTTATAT TTGG         24

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

ACTACCTGGT TGTGTGCTTT CCAT         24

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

ATCCATGAGA CTAGGTTGGT TAGGGTGGTG         30

( 2 ) INFORMATION FOR SEQ ID NO:18:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:18:

CCCTCATAGT TTAACTTTAC CTGGCTATC    29

( 2 ) INFORMATION FOR SEQ ID NO:19:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:19:

AGTGAACACC TTCTGTTTCG TGAGTC    26

( 2 ) INFORMATION FOR SEQ ID NO:20:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:20:

CGTGTGTCTT AGTTAGCTCG TGG    23

( 2 ) INFORMATION FOR SEQ ID NO:21:

( i ) SEQUENCE CHARACTERISTICS:
    ( A ) LENGTH:22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:21:

TAACGTTGTG TGTTCTGTGC TA    22

( 2 ) INFORMATION FOR SEQ ID NO:22:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:22:

AACAGATTTG GTCATATTCC TTGG    24

( 2 ) INFORMATION FOR SEQ ID NO:23:

( i ) SEQUENCE CHARACTERISTICS:
    ( A ) LENGTH: 28 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:23:

TGTGTTATGC TCCGGTAACA ATGCCCTT                28

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

AATTGTAATT TCGGTATCTC TG                      22

( 2 ) INFORMATION FOR SEQ ID NO:25:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GCAATTTCCT GTCCAATCAT TGTAG                   25

( 2 ) INFORMATION FOR SEQ ID NO:26:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

GCTTGAAGCT TTCACCCATC CTAGA                   25

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

CTTCTCCTTT ATATGTCTTA CCA                     23

( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

TATCGAGTAG ACCCTGTTGT TCGTG  25

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

CGCGTCTAGC TAAGATTTCT ACTGATGCAT  30

( 2 ) INFORMATION FOR SEQ ID NO:30:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

ATGATTTTAT GTTTATCCTG TTT  23

( 2 ) INFORMATION FOR SEQ ID NO:31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

CAGTCGCTGT ACGTGCTCTC CCTATGTAAC  30

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

CAATCGGTGT ACAATATCTT CC  22

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

CGTTAGCTGG TTAGTTAGTA CTAG  24

( 2 ) INFORMATION FOR SEQ ID NO:34:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:34:

AGGTAAGCGA TTATGGGGTT ATCG      24

( 2 ) INFORMATION FOR SEQ ID NO:35:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:35:

TAGTTACATG AACTAATCGT GGAG      24

( 2 ) INFORMATION FOR SEQ ID NO:36:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:36:

TCAATACACA AATTGATGTA CAGTGTCGAT      30

( 2 ) INFORMATION FOR SEQ ID NO:37:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:37:

CAAGCGGAAA CAATGTACAG TATTGGGATC      30

( 2 ) INFORMATION FOR SEQ ID NO:38:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:38:

GATGTACAGT ATCGCTATCG AAAGAGGCTG      30

( 2 ) INFORMATION FOR SEQ ID NO:39:

( i ) SEQUENCE CHARACTERISTICS:
  ( A ) LENGTH: 30 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:39:

GATGTACAGT ATCGCTATCG AAAGAGGCTG                30

(2) INFORMATION FOR SEQ ID NO:40:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:40:

GATGTACAGT ATCGCTATCG AAAGAGGCTG                30

(2) INFORMATION FOR SEQ ID NO:41:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:41:

GATGTACAGT ATCGCTATCG AAAGAGGCTG                30

(2) INFORMATION FOR SEQ ID NO:42:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:42:

AAGGCCATTG ATGTACAGTA TCAATGCTGC                30

(2) INFORMATION FOR SEQ ID NO:43:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:43:

AAGTGTACAG TAGTTGCCTA CGCTAGTG                28

(2) INFORMATION FOR SEQ ID NO:44:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA ( x i ) SEQUENCE DESCRIPTION: SEQ ID NO:44:

AAGTGTACAG TAGTTGCCTA CGCTAGTG                    28

( 2 ) INFORMATION FOR SEQ ID NO:45:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

AATGTGCAGT ATTGATATCG CTGGTGGTCA                  30

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

ACAATGTGAA GTATTGGGGT ACGTCAGTAG                  30

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

AATTGGGAAA CAATGTGCAG TATGTGAAGG                  30

( 2 ) INFORMATION FOR SEQ ID NO:48:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:48:

AAGTGTGCAG TAGTTACTCA TAAGAGACCA                  30

( 2 ) INFORMATION FOR SEQ ID NO:49:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

AGTGTGCAGT AGTGTGATGT CAGAGTATCC                  30

( 2 ) INFORMATION FOR SEQ ID NO:50:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:50:

AGTGTGCGGT AGTGTGATCT GAGAGTATCC                30

( 2 ) INFORMATION FOR SEQ ID NO:51:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:51:

AGTGTGTAGT AGTGTTACGA TGGGGACGG                 29

( 2 ) INFORMATION FOR SEQ ID NO:52:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:52:

AAGTGTACAG TAGTTGCCTA CGCTAGTG                  28

( 2 ) INFORMATION FOR SEQ ID NO:53:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:53:

AGTGTACAGT AGTGTTCCCG GTAGAGCTAT                30

( 2 ) INFORMATION FOR SEQ ID NO:54:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:54:

AAATGGGAAA CAATGTGCAG TATTGGAAGG                30

( 2 ) INFORMATION FOR SEQ ID NO:55:

( i ) SEQUENCE CHARACTERISTICS:
      ( A ) LENGTH: 30 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:55:

AAGACCAGAC AATGTACAGT ATTGGCCTGA  30

( 2 ) INFORMATION FOR SEQ ID NO:56:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:56:

AGGTGGGACA TTCTTTGCGT TATGTCTCTG A  31

( 2 ) INFORMATION FOR SEQ ID NO:57:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:57:

AGGAATCTGG GGCATTCTTT GCGTTTGCG  29

( 2 ) INFORMATION FOR SEQ ID NO:58:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:58:

GATCATCTCA GAGCATTCTT AGCGTTTTGT  30

( 2 ) INFORMATION FOR SEQ ID NO:59:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:59:

GAGAACTCCG TTCTTAGCGT ATTGGAGTCC  30

( 2 ) INFORMATION FOR SEQ ID NO:60:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:60:

GATCATCTAA GAGCATTCTT AGCGTTTTGG 30

( 2 ) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:61:

GGGCTCGGAA CATTCTTAGC GTTTTGTTCC 30

( 2 ) INFORMATION FOR SEQ ID NO:62:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:62:

CAAAACGAGA GAGCTTTCTG TGCGTTTAGC 30

( 2 ) INFORMATION FOR SEQ ID NO:63:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:63:

AATTGAAGTG ACTTTCTCTG CGTTTAGTCG 30

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:64:

AATCGATTGT TGAACATTCT GACGTTTTGT 30

( 2 ) INFORMATION FOR SEQ ID NO:65:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:65:

AATCGATTGT TGAACATTCT GACGTTTTGT 30

( 2 ) INFORMATION FOR SEQ ID NO:66:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:66:

AGAAGCATAC GAAGACATTC CAACGTTTTG     30

( 2 ) INFORMATION FOR SEQ ID NO:67:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:67:

AGAAGCATAC GAAGACATTC CAACGTTTTG     30

( 2 ) INFORMATION FOR SEQ ID NO:68:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:68:

CTCAGGATAA GGTCATTCTA ACGTTATGA     29

( 2 ) INFORMATION FOR SEQ ID NO:69:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:69:

GACCAAGCGT CAAGATATTC AAACGTTTTA     30

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:70:

AGAAGCATAC GAAGACATTC CAACGTTTGG     30

( 2 ) INFORMATION FOR SEQ ID NO:71:

( i ) SEQUENCE CHARACTERISTICS:
        ( A ) LENGTH: 29 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:71:

TACGCTGACA GGCCACGTTT TGTCATGAT    29

(2) INFORMATION FOR SEQ ID NO:72:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:72:

ATAGGCAGGG GACATTGCAA CCTTTTGTCA    30

(2) INFORMATION FOR SEQ ID NO:73:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:73:

CATTGGGCCA GAGGAACACA ACCTCAACAG    30

(2) INFORMATION FOR SEQ ID NO:74:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:74:

ATGCCTAAGT TTCGAACGCG GCTAGCCAGC TTTTGCTGGC TAGCCGCGTT    50

CGAAACTTAG GCAT    64

NUCLEIC ACID LIGAND INHIBITORS TO DNA POLYMERASES

RELATED APPLICATIONS

This application is a Continuation-in-Part of U.S. patent application Ser. No. 07/714,131, filed Jun. 10, 1991, entitled Nucleic Acid Ligands, now U.S. Pat. No. 5,475,096 which is a Continuation-in Part of U.S. patent application Ser. No. 07/536,428, filed Jun. 11, 1990, entitled Systematic Evolution of Ligands by Exponential Enrichment, now abandoned; and U.S. patent application Ser. No. 07/964,624, filed Oct. 21, 1992, entitled Nucleic Acid Ligands now U.S. Pat. No. 5,496,938.

FIELD OF THE INVENTION

Described herein are methods for identifying and preparing high-affinity nucleic acid ligands to DNA polymerases, specifically those isolated from *Thermus aquaticus* (Taq polymerase) and *Thermus thermophilus* (Tth polymerase). The method utilized herein for identifying such nucleic acid ligands is called SELEX, an acronym for Systematic Evolution of Ligands by EXponential Enrichment. Also described herein is an improved method for performing the Polymerase Chain Reaction using the nucleic acid ligands of this invention. Specifically disclosed herein are high-affinity nucleic acid ligands to Taq polymerase and Tth polymerase. The invention includes high-affinity DNA ligands which bind to Taq polymerase and Tth polymerase, thereby inhibiting their ability to polymerase DNA synthesis at ambient temperatures.

BACKGROUND OF THE INVENTION

The Polymerase Chain Reaction (PCR), is a recently developed technique which has had a significant impact in many areas of science. PCR is a rapid and simple method for specifically amplifying a target DNA sequence in an exponential manner. Briefly, the method consists of synthesizing a set of primers that have nucleotide sequences complementary to the DNA that flanks the target sequence. The primers are then mixed with a solution of the target DNA, a thermostable DNA polymerase and all four deoxynucleotides (A, T, C and G). The solution is then heated to a temperature sufficient to separate the complementary strands of DNA (approximately 95° C.) and then cooled to a temperature sufficient to allow the primers to bind to the flanking sequences. The reaction mixture is then heated again (to approximately 72° C.) to allow the DNA synthesis to proceed. After a short period of time the temperature of the reaction mixture is once again raised to a temperature sufficient to separate the newly formed double-stranded DNA, thus completing the first cycle of PCR. The reaction mixture is then cooled and the cycle is repeated. Thus, PCR consists of repetitive cycles of DNA melting, annealing and synthesis. Twenty replication cycles can yield up to a million fold amplification of the target DNA sequence. The ability to amplify a single DNA molecule by PCR has applications in environmental and food microbiology (Wernars et al. (1991) Appl. Env. Microbiol. 57:1914–1919; Hill and Keasler (1991) Int. J. Food Microbiol. 12:67–75), clinical microbiology (Wages et al. (1991) J. Med. Virol. 33:58–63; Sacramento et al. (1991) Mol. Cell Probes 5:229–240), oncology (Kumar and Barbacid (1988) Oncogene 3:647–651; McCormick (1989) Cancer Cells 1:56–61), genetic disease prognosis (Handyside et al. (1990) Nature 344:768–770), blood banking and forensics (Jackson (1990) Transfusion 30:51–57).

The availability of thermostable DNA polymerases such as Taq DNA polymerase has both simplified and improved PCR. Originally only heat-sensitive polymerases, such as *E. coli* DNA polymerase were available for use in PCR. Heat-sensitive polymerases, however, are destroyed at the temperatures required to melt double-stranded DNA, and additional polymerase has to be added after each PCR cycle. Taq DNA polymerase, isolated from the thermophilic bacterium *Thermus aquaticus,* is stable up to 95° C. and its use in PCR has eliminated the necessity of repetitive addition of temperature sensitive polymerases after each thermal cycle. Additionally, because Taq polymerase can be used at higher temperatures it has improved the specificity and sensitivity of PCR. The reason for the improved specificity is that at higher temperatures the binding of promoters to sites other that the desired ones (referred to as mispriming) is significantly reduced.

Since its discovery, the Polymerase Chain Reaction has been modified for various applications, such as in situ PCR, in which the detection limit of traditional in situ hybridization has been pushed to the single copy level (Haase et al. (1990) Proc. Natl. Acad. Sci., USA 87:4971–4975), and reverse transcriptase PCR (RT-PCR), wherein an RNA sequence is converted to its copy DNA (cDNA) by reverse transcriptase (RT) before being amplified by PCR, making RNA a substrate for PCR (Kawasaki (1991) Amplification of RNA in *PCR Protocols, A Guide to Methods and Applications,* Innis et al., Eds. Academic Press Inc., San Diego, Calif., 21–27). Mesophilic viral reverse transcriptases, however, are often unable to synthesize full-length cDNA molecules because they cannot "read through" stable secondary structures of RNA molecules. This limitation has recently been overcome by use of a polymerase isolated from *Thermus thermophilus* (Tth polymerase). Tth polymerase is a thermostable polymerase that can function as both reverse transcriptase and DNA polymerase (Myers and Gelfand (1991) Biochemistry 30:7662–7666). The reverse transcription performed at an elevated temperature using Tth polymerase eliminates secondary structures of template RNA, making it possible for the synthesis of full-length cDNA.

Although significant progress has been made in PCR technology, the amplification of nontarget oligonucleotides due to side-reactions, such as mispriming of background DNA and/or primer oligomerization still presents a significant problem. This is especially true in diagnostic applications in which PCR is carried out in a milieu containing background DNA while the target DNA may be present in a single copy (Chou et al. (1992) Nucleic Acid Res. 20:1717–1723). It has been determined that these side reactions often occur when all reactants have been mixed at ambient temperature before thermal cycling is initiated.

Two methods have been reported which minimize these side reactions. In the first method, termed "hot start" PCR (Chou et al. (1992) Nucleic Acid Res. 20:1717–1723; D'Aquila et al. (1991) Nucleic Acid Res. 19:3749), all of the reagents are heated to 72° C. before adding the final reagent, usually the polymerase. Although this method does increase specificity, thereby reducing side products, the method is inconvenient for dealing with a large number of samples, the reaction mixture can become more easily contaminated, and the method is error-prone.

In the second method, a neutralizing antibody to Taq (referred to as TaqStart) is added to the complete reaction mixture. This antibody inhibits the polymerase activity at ambient temperature (Kellogg et al. (1994) Biotechniques 16:1134–1137), but is inactivated by heat denaturation once the reaction is thermocycled, rendering the polymerase active. The drawback of this approach to reducing side products is that the anti-Taq antibody should be stored at −20° C. until use, which means that detection kits should be packaged and shipped under controlled environment adding to their cost. In addition, a significant amount of antibody (~1 μg of antibody/5 U of Taq) is needed for a single PCR.

The development of high affinity nucleic acid ligands capable of inhibiting the thermostable Taq and Tth polymerases would obviate the need for the "hot start" method and would overcome the limitations associated with the second method. Nucleic acid inhibitors can be developed that are extremely specific and have high affinity. Since nucleic acids are more stable than proteins at ambient temperature, the shipping and packaging problems associated with using antibodies can be overcome. Additionally, nucleic acids, like antibodies will lose their affinity for the polymerase at higher temperatures, allowing the polymerase to be activated when desired. The potential for mispriming mediated by nucleic acid based inhibitors themselves functioning as primers (in addition to the specific primers used in the reaction) in PCR can be eliminated by capping their 3' ends.

BRIEF SUMMARY OF THE INVENTION

The present invention includes methods of identifying and producing nucleic acid ligands to DNA polymerases. Specifically included are methods for identifying nucleic acid ligands to thermostable DNA polymerases useful in the Polymerase Chain Reaction, including the Taq and Tth polymerases and the nucleic acid ligands so identified and produced. More particularly, DNA sequences are provided that are capable of binding specifically to the Taq and Tth polymerases respectively, thereby inhibiting their ability to catalyze the synthesis of DNA at ambient temperatures.

Further included in this invention is a method of identifying nucleic acid ligands and nucleic acid ligand sequences to the Taq and Tth polymerases comprising the steps of (a) preparing a candidate mixture of nucleic acids, (b) partitioning between members of said candidate mixture on the basis of affinity to the Taq or Tth polymerases, and (c) amplifying the selected molecules to yield a mixture of nucleic acids enriched for nucleic acid sequences with a relatively higher affinity for binding to the Taq and Tth polymerases, respectively.

Further included in this invention is an improved method of performing the Polymerase Chain Reaction comprising the step of including a nucleic acid ligand that inhibits the thermostable polymerase at ambient temperatures but dissociates from the polymerase at elevated temperatures. Such nucleic acid ligands are identified according to the method of this invention.

More specifically, the present invention includes the ssDNA ligands to Taq polymerase and Tth polymerase identified according to the above-described method, including those ligands listed in Tables 2 and 3 (SEQ ID NOS:6–73). Also included are DNA ligands to Taq polymerase and Tth polymerase that are substantially homologous to any of the given ligands and that have substantially the same ability to bind and inhibit the activity of Taq polymerase and Tth polymerase. Further included in this invention are DNA ligands to Taq polymerase and Tth polymerase that have substantially the same structural form as the ligands presented herein and that have substantially the same ability to bind and inhibit the activity of Taq polymerase and Tth polymerase.

The present invention also includes modified nucleotide sequences based on the DNA ligands identified herein and mixtures of the same.

BRIEF DESCRIPTION OF THE FIGURES

FIG. 4A illustrates a polymerase activity assay for the Taq and Tth polymerases carried out at different temperatures with different times of incubations. The DNA is resolved on a 15% polyacrylamide gel under denaturing conditions. The data on Panel A were obtained with the Taq polymerase and the enriched pool selected for Taq, whereas those shown on Panel B were obtained with the Tth polymerase and the enriched pool selected for Tth. The untreated, 5'-end labeled DNA hairpin template (lane 1); the labeled template in a reaction mixture that lacks the polymerase (lane 2); incubation of the complete reaction mixture for 25 minutes at room temperature in the absence of (lane 3) and in the presence of the enriched pool (lane 4). Lanes 5, 6, and 7 shows the incubations of complete reaction mixtures in the presence of the enriched pool for 5 minutes at 37° C., 50° C. and 60° C., respectively. Lanes 8 and 9 show the incubations of the complete reaction mixtures in the presence (lane 8) and absence (lane 9) of the enriched pool at 70° C. for 5 minutes. Lane 10 shows the gel mobility of the end-labeled pool DNA. The schematics on right depict the positions of the starting short end-labeled DNA and the polymerase extended product.

FIGS. 4B and 4C illustrate a second polymerase activity assay for the Taq and Tth polymerases, performed at three different temperatures. The DNA is resolved on a 15% polyacrylamide gel under denaturing conditions. The data in FIG. 4B was obtained with the Taq polymerase and the data on FIG. 4C was obtained with the Tth polymerase. Lanes 1–3 show the products obtained in the absence of any inhibitor upon incubation at room temperature, 30° C. and 37° C., respectively, for 5 minutes. Lanes 4–6 show the data obtained with the unselected random sequence pool; lanes 7–9 with the enriched pool for Taq; lanes 10–12 with the enriched pool for Tth; lanes 13–15 with Taqstart antibody for 5 minutes incubations at the three temperatures indicated. The schematics on right indicates the starting short end-labeled DNA and the polymerase extended product.

FIGS. 4D and 4E illustrate a third polymerase activity assay for the Taq and Tth polymerases, resolved on a 15% polyacrylamide gel under denaturing conditions. FIG. 4D shows the activity of Taq in the presence of the enriched pool that has not been subjected to thermal cycling, whereas FIG. 4E exhibits the activity of Taq in the presence of the enriched pool that has been thermal cycled. Lanes 1–5 indicate the amount of product formed over 5 minute incubations at 20° C., 25° C., 30° C., 35° C. and 40° C., respectively. Lanes 6–10 exhibit Taq activity in the presence of the enriched pool over 5 minute incubations at 20° C., 25° C., 30° C., 35°

Figure 1A:
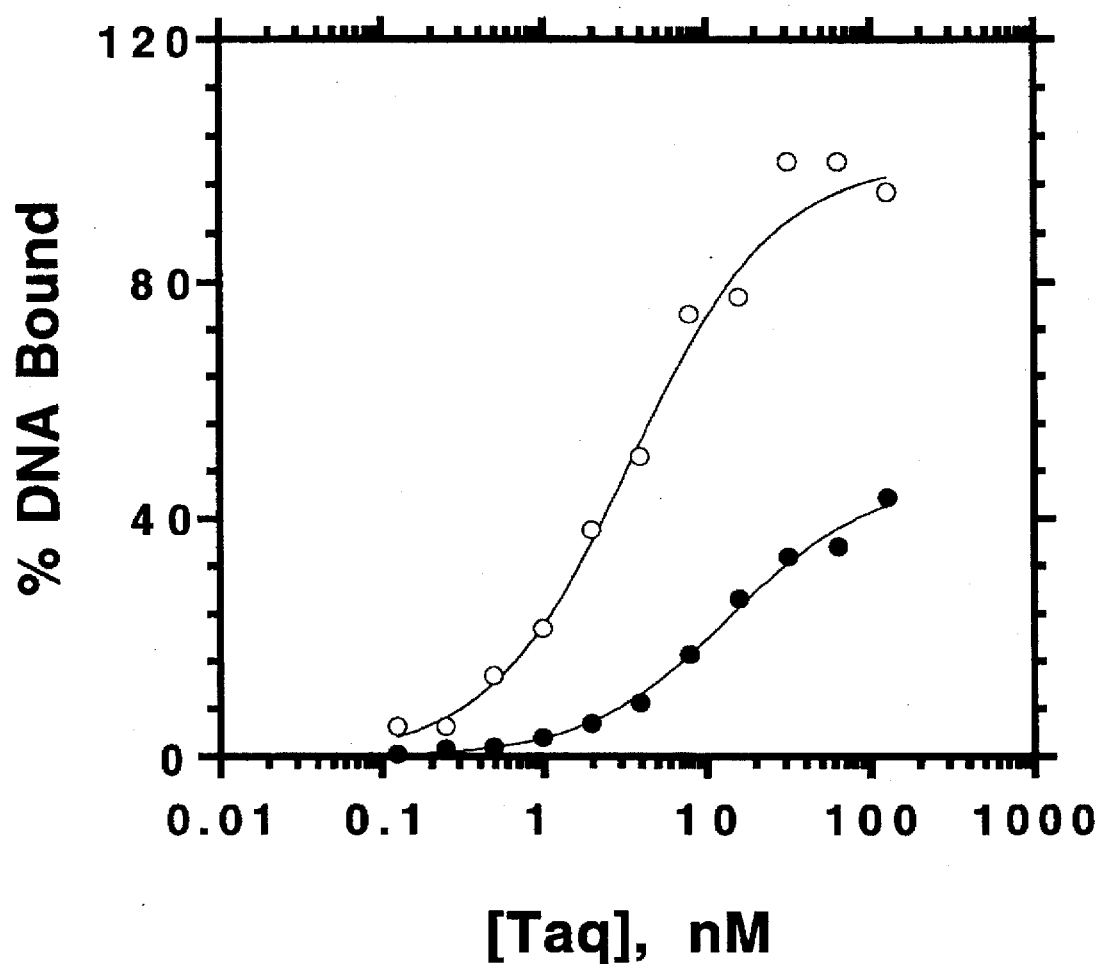
FIG. 1A shows the binding affinities of enriched pools of DNA after 12 rounds of SELEX (○) and the unselected random pool (●) of DNA for the Taq polymerase.

C. and 40° C., respectively. The schematics on right depict the starting short end-labeled DNA and the polymerase extended product.

DETAILED DESCRIPTION OF THE INVENTION

This application describes the isolation of nucleic acid ligands to DNA polymerases, specifically the thermostable polymerases useful in the Polymerase Chain Reaction. Taq polymerase and Tth polymerase, identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands now U. S. Pat. No. 5,475,096 and U.S. patent application Ser. No. 07/931,473, filed Aug. 17, 1992, entitled methods for identifying Nucleic Acid Ligands, now U.S. Pat. No. 5,270,163, (see also WO 91/19813, published Dec. 26, 1991). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific targets of nucleic acid inhibitors of the Taq and Tth polymerases. In the Example section below, the experimental parameters used to isolate and identify the nucleic acid inhibitors to the Taq and Tth polymerases are described.

In co-pending and commonly assigned U.S. patent application Ser. No. 07/964,624, filed Oct. 21, 1992 (1938 patent), methods are described for obtaining improved nucleic acid ligands after SELEX has been performed. The (1938 patent), entitled Nucleic Acid Ligands to HIV-RT and HIV-1REV is specifically incorporated herein by reference.

In the present invention, a SELEX experiment was performed in order to identify nucleic acid ligands with specific high affinity for the Taq and Tth polymerases from a degenerate library containing 30 random positions (30N). Although RNA or DNA ligands could be identified for this purpose, the examples below describe the identification of DNA ligands. This invention includes the specific ssDNA ligands to Tth polymerase shown in Table 2 (SEQ ID NOS:6-35) and Taq polymerase shown in Table 3 (SEQ ID NOS:36-73), identified by the methods described in Example 1.

The scope of the ligands covered by this invention extends to all nucleic acid ligands of the Taq and Tth polymerases, modified and unmodified, identified according to the SELEX procedure. More specifically, this invention includes nucleic acid sequences that are substantially homologous to the ligands shown in Tables 2 and 3. By substantially homologous it is meant a degree of primary sequence homology in excess of 70%, most preferably in excess of 80%. A review of the sequence homologies of the ligands of Taq and Tth shown in Tables 2 and 3 shows that sequences with little or no primary homology may have substantially the same ability to bind Taq and Tth, respectively. For these reasons, this invention also includes nucleic acid ligands that have substantially the same ability to bind the Taq and Tth polymerases as the nucleic acid ligands shown in Tables 2 and 3. Substantially the same ability to bind Taq or Tth means that the affinity is within a few orders of magnitude of the affinity of the ligands described herein. It is well within the skill of those of ordinary skill in the art to determine whether a given sequence—substantially homologous to those specifically described herein—has substantially the same ability to bind Taq and Tth, respectively.

This invention also includes the ligands as described above, wherein certain chemical modifications are made in order to increase the in vivo or in vitro stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 8, 1993, entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process.

The nucleic acid ligands to the Taq and Tth polymerases described herein are useful as reagents in the Polymerase Chain Reaction.

The present invention includes an improved method for performing the Polymerase Chain Reaction, wherein a sample containing a nucleic acid sequence that is to be amplified is mixed with 1) primers that are complementary to sequences that flank the sequence to be amplified, 2) a thermostable polymerase, and 3) a nucleic acid ligand that is capable of inhibiting the polymerase at ambient temperatures. The normal steps of PCR are then followed—melting, annealing and synthesis—by thermal cycling of the mixture. The presence of the nucleic acid ligand prevents the mixture from amplifying background DNA by preventing any synthesis at lowered temperatures prior to or during cycling. The present invention also includes a PCR kit comprising a thermostable DNA polymerase and a nucleic acid ligand that inhibits said polymerase at ambient temperatures yet allows synthesis to occur during the elevated temperature cycles of the PCR process. The present invention also includes a method for improving PCR, as understood by those skilled in the art, including the step of adding to the thermostable polymerase a nucleic acid ligand that inhibits said polymerase at ambient temperatures yet allows synthesis to occur during the elevated temperature cycles of the PCR process.

The following Examples are provided to explain and illustrate the present invention and are not intended to be limiting of the invention.

Example 1 describes the experimental procedures used in the selection of nucleic acid ligands to both the Taq and Tth polymerases. Example 2 describes the polymerase inhibition assay and demonstrates that the ligands of the invention are capable of inhibiting the interaction of both the Taq and Tth polymerases.

In Example 2 the designed hairpin DNA (DNA-HP; 5'-ATGCCTAAGTTTCGAACGCGGCTAGCCAGCTTT-TGCTGGCTAGCCGCGT-3' (SEQ ID NO:6) was used as the template for measurement of the ability of the enriched pools of DNA to inhibit polymerase activity. In these inhibition assays 0.25 pmoles of Taq (5 U) and 0.25 pmoles of Tth (2.5 U) are used in 20 µL reaction volume. These quantities of enzymes are about five times higher than what would be typically used in PCR reactions. The amount of ssDNA nucleic acid ligand added (5 pmoles) was 20 times greater than the amount of polymerase used in these assays. FIG. 4A shows the results of inhibition assay carried out at different temperatures with different times of incubations. The activity of both the Taq and Tth polymerases is generally low at low temperatures and increases as the temperature is increased, as can be seen by comparing lane 3 (room temperature reaction) with lanes 6–9 (reaction at 50°, 60° and 70°C., respectively). The enriched pools inhibit the activity of their respective polymerases at room temperature (lane 4), but not at 50°C.–70° C. Lane 10 shows the mobility of the radiolabeled pool as a reference to detect the possible extension of DNA molecules in the pool that can serve as a template for the polymerases. The lack of radiolabeled bands migrating closer or above the labeled pool in lanes 6–9 indicates the absence of polymerization of the ssDNA pool.

Since the activity of thermostable polymerases is low at ambient temperature, the incubation period in the assay was increased to 16 hours. FIGS. 4B and 4C show the results of 16 hour incubation of the template with the two polymerases in the presence of selected pools and the random pool. In addition, the inhibition mediated by selected pools was compared to that of anti-Taq antibody (TaqStart). Over the three temperatures studied, room temperature, 30° C. and 37° C., the random pool did not show inhibition of the two polymerases (compare lanes 1–3 with 4–6), suggesting that the inhibition caused by the enriched pool is sequence specific. The pool selected for Taq completely inhibited the polymerase activity over 16 hour incubation only at room temperature (lane 7), but not at 30° C. and above (lanes 8 & 9). Although the pool selected for Tth did show binding to Taq, it was unable to inhibit Taq (lanes 10–12). As expected, Taqstart antibody inhibited the polymerase activity at all three temperatures investigated (lanes 12–15). The ssDNA pool selected for Tth, however, did not inhibit the enzyme activity over 16 hour incubation (compare lanes 1–3 with 4–6). In contrast, the same pool was able to inhibit the enzyme activity over short periods of incubation. The pool selected for Taq polymerase was able to partially inhibit (>50%) the Tth activity over 16 hour incubation at room temperature (lane 10). Taqstart antibody did not have any effect on the activity of Tth (lanes 13–15).

The use of Taqstart antibody is limited to one time in a PCR reaction. Once it is denatured at high temperature it cannot renature back to its native form. Nucleic acid ligands with simple secondary structures, however, have the potential to renature back to their native form after going through a heat cycle. An experiment was carried out to investigate whether the inhibitory capacity of the DNA pool selected for Taq polymerase can be restored after heating (FIGS. 4D and 4E). FIG. 4D shows the inhibition of Taq activity between 20° C.–40° C. by the selected DNA pool that has not been subjected to heat cycling. Over 45 minutes of incubation, the pool completely inhibits Taq activity at 20° C. and 25° C. Within this relatively short period of incubation, the pool exhibited >70% inhibition at 30° C. A very similar inhibition profile can be seen with the DNA pool that has been subjected to two PCR cycles with the Taq polymerage in the absence of the template DNA. This result demonstrates that the inhibition mediated by ssDNA can be restored even after PCR.

EXAMPLE 1.

EXPERIMENTAL PROCEDURES

A. Materials and Methods

Recombinant Taq polymerage (rTaq; Mr 94 kDa) suspended in a buffer consisting of 100 mM KCl, 20 mM Tris-HCl (pH 8.0), 0.1 mM EDTA, 50 % glycerol (v/v) and 0.2% Tween 20 and recombinant Tth polymerage (rTth Mr 94 kDa) suspended in a buffer consisting of 50 mM Bicine-KOH (pH 8.3), 90 mM KCl and 50% glycerol (v/v) were purchased from Roche Molecular Systems, Inc. (Alameda, Calif.). Deoxyoligonucleotides were synthesized by standard cyanoethyl phosphoramidite chemistry and purified by denaturing polyacrylamide gel electrophoresis to size homogeneity before used. All other reagents and chemicals were purchased from standard commercial sources.

B. SELEX.

The SELEX procedure has been described in detail in U.S. Pat. No. 5,270,163. The SELEX experiments on both polymerases were performed using the template and primers shown in Table 1. The selection on Taq polymerage was carried out in a buffer consisting of 10 mM Tris-HCL (pH 8.3; at 25° C.), 50 mM KCl and 2.5 mM $MgCl_2$ (Taq binding buffer). The selection on Tth polymerase was carried out in a buffer containing 50 mM Bicine-KOH (pH 8.3; at 25° C.), 90 mM KCl and 3.5 mM $Mn(OAc)_2$ (Tth binding buffer).

Each SELEX experiment was initiated with 5 nmoles of synthetic, gel-purified random sequence pool single stranded DNA (ssDNA) consisting of 30 nucleotide randomized region, flanked by 5' and 3' regions of fixed structure (Table 1). In a typical round of selection, ssDNA suspended in the appropriate binding buffer was heated to 90° C. for 3 minutes, chilled on ice, and then brought to room temperature. Once equilibrated at room temperature, the DNA was incubated for 15 minutes with the appropriate target polymerase in the presence of 2 nmoles of tRNA as a competitor. After incubating, hSA was added to the reaction mixture to a final concentration of 0.01%. Polymerase-DNA complexes were separated from unbound DNA by nitrocellulose filtration through a prewet nitrocellulose filter (0.45 µM) under suction. The filter was immediately washed with 20 mL of the binding buffer, 20 mL of 0.5M urea in the binding buffer, and 0.5M urea in water. Bound DNA was isolated from the filters by elution and precipitation from ethanol in the presence of carrier tRNA (5 µg).

The isolated DNA was amplified by PCR with Primer Set I (Table 1). One of the primer strands contained three contiguous biotins at the 5end. The unbiotinylated strand of the resulting duplex DNA was isolated by gel electrophoresis under denaturing conditions and used for the next round of selection. In subsequent rounds, prior to incubating with the target polymerase, DNA pools were passed through nitrocellulose filters (counter selection) to remove DNA sequences that bind to the nitrocellulose filter. The number of picomoles of target polymerase was gradually decreased during the course of SELEX to increase the selective pressure on positive selection. The amount of DNA in each selection was kept at least five-fold higher than the amount of protein to ensure competition for high affinity binding DNA sequences.

The progress of SELEX was monitored by nitrocellulose filter binding analysis of enriched pools. The enriched pools that showed the highest affinity binding was PCR amplified with Primer Set II to incorporate BamHI and ECoRI restriction sites at the termini of the resulting duplex DNA. This DNA was gel purified and digested with BamHI and ECoRI and cloned into plasmid pUC18 vector previously digested with the same enzymes using standard techniques. Clones were isolated and sequenced by standard dideoxy sequencing technique (Sequenase kit from U.S. Biochemical, Cleveland, Ohio).

C. Nitrocellulose Filter Partitioning.

For isolation of DNA molecules that bind tightly to Taq polymerase and Tth polymerase, respectively, the nitrocellulose filter partitioning method was used as described in the SELEX Patent Applications. Briefly, gel-purified $^{32}P$ ss-DNA pools labeled at the 5' end were suspended in the binding buffer, heated to 80° C., chilled on ice and then brought to room temperature. The DNA was then incubated for 15 minutes at room temperature with varying amounts of the target polymerase in 50 µL of the appropriate binding buffer containing 0.1 µg of tRNA and 0.01% hSA. The DNA concentrations were kept lower than 100 pM to ensure equilibrium in the presence of excess protein concentrations. After 15 minutes the binding reaction mixtures were passed through pre-wet nitrocellulose/cellulose acetate mixed matrix filters (0.45 µm pore size, Millipore Corporation, Bedford, Mass.) and the filters were immediately washed with 5 mL of binding buffer. The amount of DNA bound to the filters was quantitated by measuring the radioactivity of the filters by liquid scintillation counting. The quantity of DNA bound to filters in the absence of protein was used for background correction. The percentage of input DNA retained on each filter was plotted against the corresponding log of the protein concentration (FIGS. 1 and 2). The nonlinear least square method was used to obtain the dissociation constants ($K_d$) of the DNA ligands to the Taq and Tth polymerases respectively (Jellinek et al. (1993) Proc. Natl. Acad. Sci., U.S.A. 90:11227–11231).

Figure 1B:
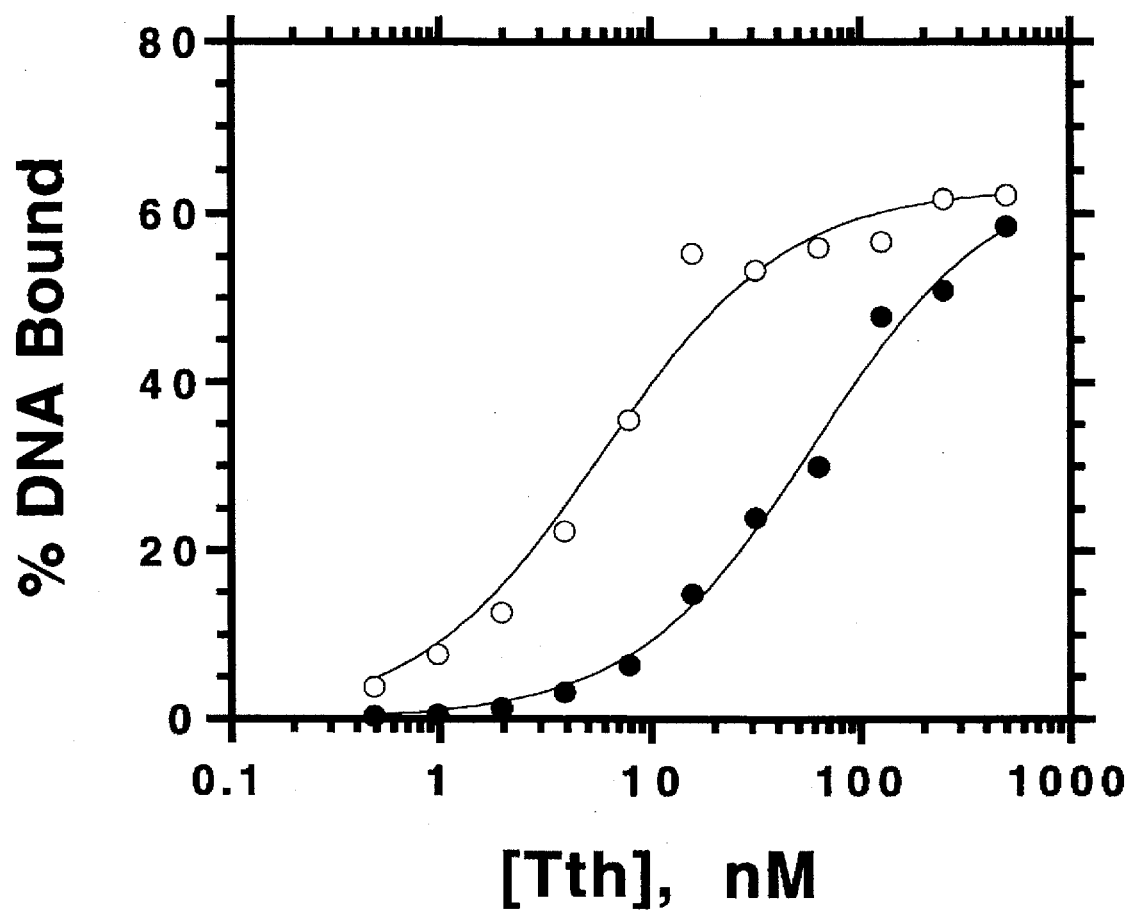
FIG. 1B shows the binding affinities of enriched pools of DNA after 10 rounds of SELEX (○) and the unselected random pool (●) of DNA for the Tth polymerase.

The unselected random sequence pool bind Tth polymerase with an estimated $K_d$ of approximately 70 nM (FIG. 1B (●)), whereas the $K_d$ of this pool binding to Taq polymerase is >50 nM (FIG. 1A, (○)). After 12 rounds of selection, the $K_d$ of binding to Taq was 3.5 nM (FIG. 1A,(○)). Additional rounds of selection did not result in further improvement of affinity. Thus, the resulting affinity of the enriched pool to Taq polymerase was significantly improved as compared to the unselected random pool. Similar results were obtained with the Tth polymerase where the pool from the 10th round showed a $K_d$ of 5 nM (FIG. 1B, ○)).

Figure 2A:
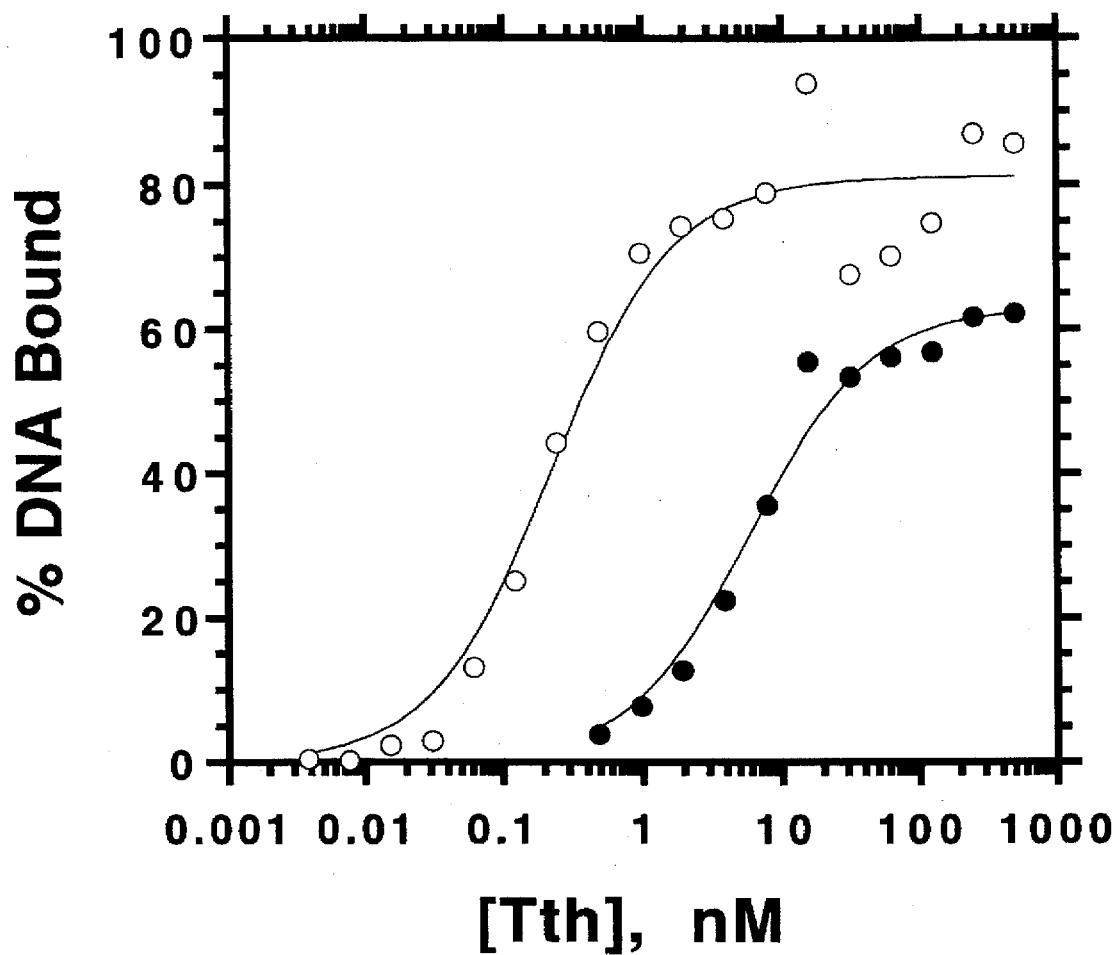
FIG. 2A shows a cross binding analysis of the enriched DNA pool for the Taq polymerase (○) and the enriched DNA pool for the Tth polymerase (●) to the Tth polymerase.
Figure 2B:
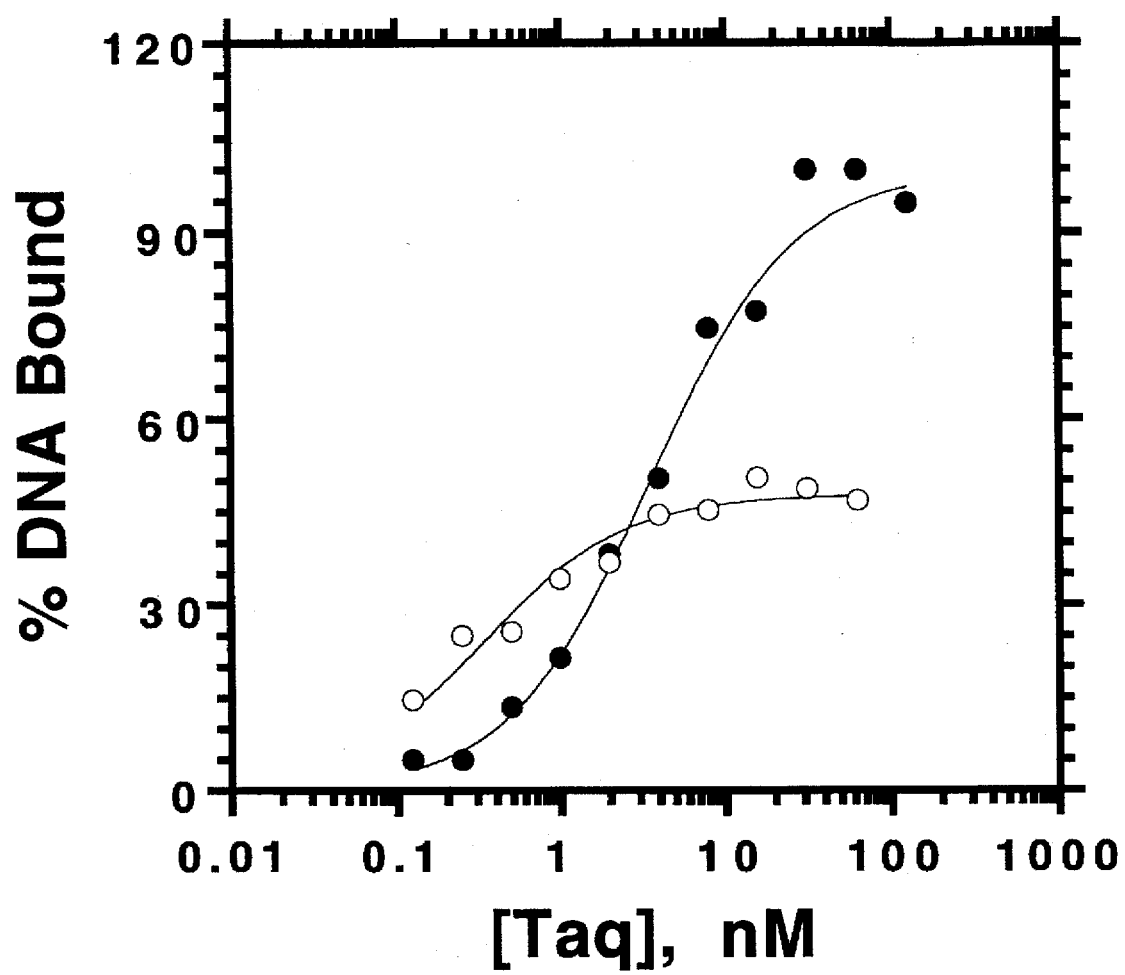
FIG. 2B shows a cross binding analysis of the enriched DNA pool for the Taq polymerase (○) and the enriched DNA pool for the Tth polymerase (●) to the Taq polymerase.

The ssDNA pool selected for Taq polymerase showed very tight binding to Tth polymerase with a $K_d$ of 0.2 nM (FIG. 2A, (○)). This result is not surprising, since the amino acid sequence identity between the two polymerases is approximately 87% (Asakura et al. (1993) J. Ferment. Bioeng. 76:265–269). The pool selected for Tth polymerase bound Taq polymerase in a different manner, with the binding saturating at around the 50% level (FIG. 2B (○)), suggesting that about one half of the sequences in the pool are not interacting with Taq polymerase. Based on 50% saturation the estimated $K_d$ is 0.3 nM.

The ss-DNA sequences obtained from 12 rounds of selection performed with Taq polymerase and 10 rounds of selection performed with Tth polymerase are set forth in Tables 2 and 3. Thirty nine individual clones were sequenced from the Taq polymerase selection and 29 individual clones were sequenced from the Tth polymerase selection (only the variable 30 nucleotide region is shown). The ligands were grouped into classes based upon primary sequence homology.

EXAMPLE 2.

POLYMERASE INHIBITION ASSAY

Figure 3:
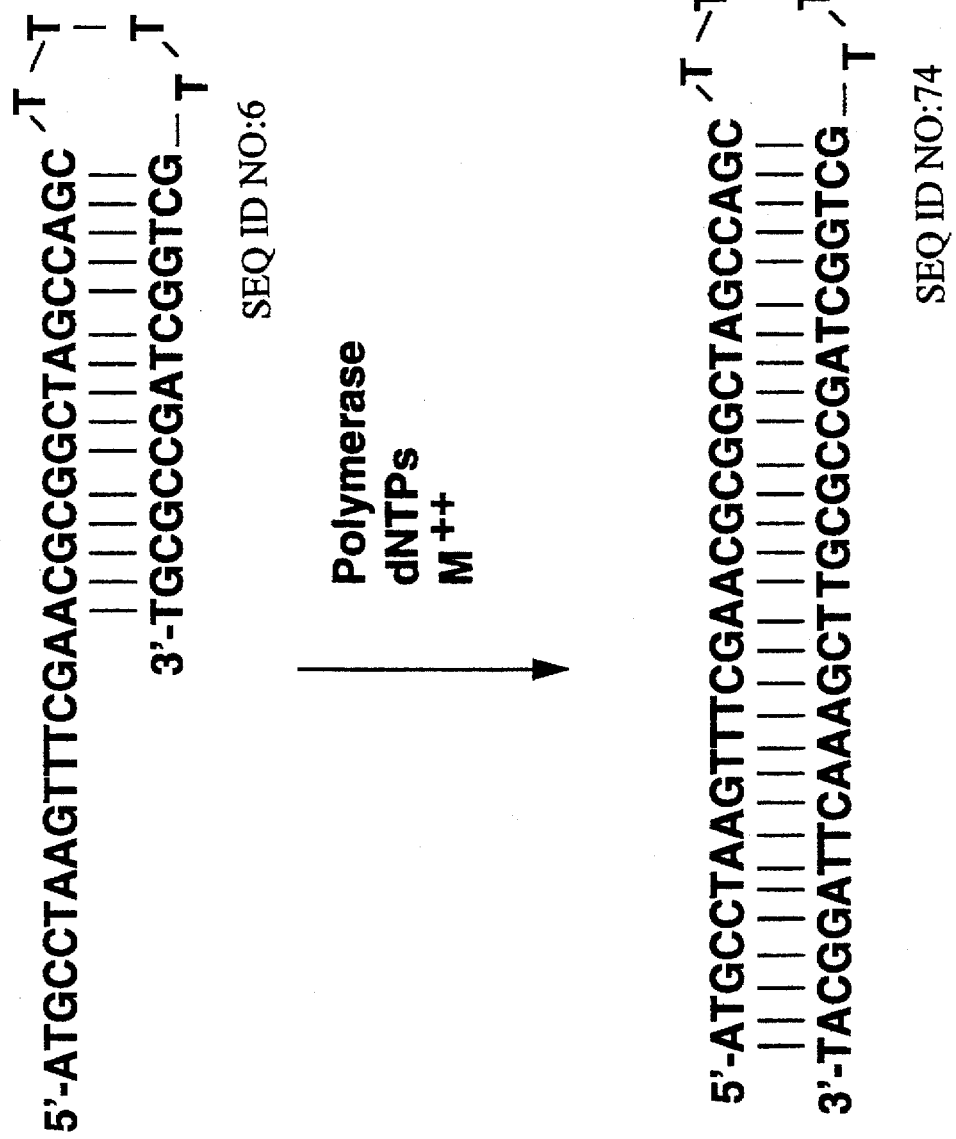
FIG. 3 illustrates the DNA polymerization.
Figure 5A:
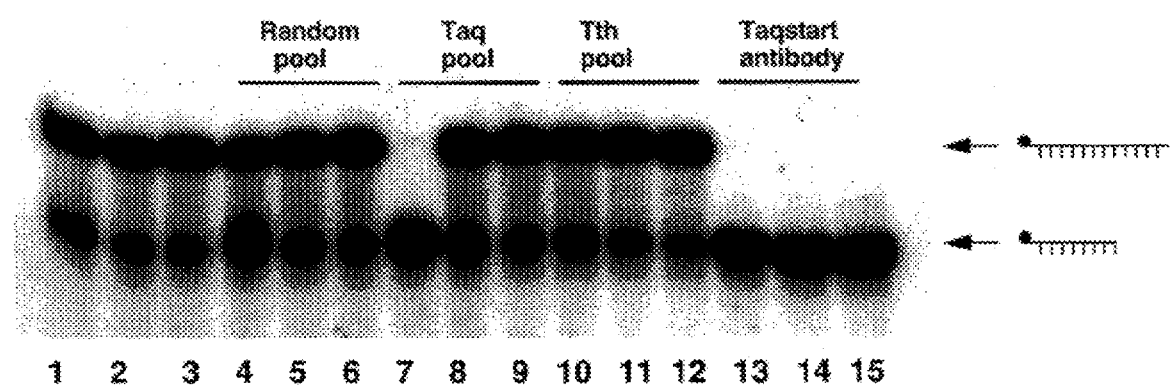
Figure 5B:
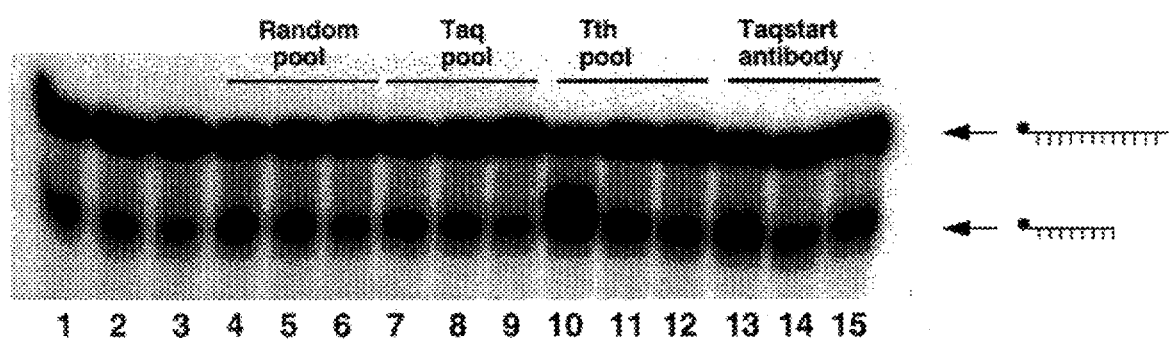

The polymerase inhibition assays were performed using the template DNA (DNA-HP; 5'-ATGCCTAAGTTTCGAACGCGGCTAGCCAGCTTT-TGCTGGCTAGCCGCGT-3' (SEQ ID NO:6)), end-labeled at the 5' end with T4 polynucleotide kinase and $^{32}P$-γ-ATP and purified by gel electrophoresis under denaturing conditions (FIG. 3). In a representative experimental procedure, 0.25 pmoles of Taq polymerase (5 U) was mixed with 5 pmoles of the enriched pool (or the random pool) in the standard PCR buffer. 3 pmoles of labeled template DNA was added and the mixture was incubated at different temperatures for a given period of time. The reaction was stopped by adding EDTA to a final concentration of 125 mM (5 µL of 0.5 M EDTA). The DNA was resolved on a 15% polyacrylamide gel under denaturing conditions. FIGS. 4A–4E illustrate the results of the polymerase activity assays.

Starting Random Sequence Pool of ssDNA:

5'-TTCTCGGTTGGTCTCTGGCGGAGC-[N]$_{30}$-TCTTGTGTATGATTCGCTTTTCCC-3'
(SEQ ID NO:1)

SELEX PCR Primer Set I:

5'-TTCTCGGTTGGTCTCTGGCGGAGC-3'   (SEQ ID NO:2)

5'-BBBTAGGGAAAAGCGAATCATACACAAGA-3'   (SEQ ID NO:3)

(B represents Biotin)

SELEX PCR Primer Set II:

5'-GGCG<u>GAATTC</u>TTCTCGGTTGGTCTCTGGCGGAGC-3'
     EcoRI   (SEQ ID NO:4)

5'-CGC<u>GGATCC</u>TAATACGACTCACTATAGGGAAAAGCGAATCATACACAAGA-3'
    BamHI   (SEQ ID NO:5)

TABLE 2

Sequences derived from the selection for Tth polymerase

| SEQ ID NO: | CLONE NO: | SEQUENCE (5'-3') | | |
|---|---|---|---|---|
| CLASS I | | | | |
| 7 | 2: | TATCGTTTACTCATT | GTTTTG | TGTGT |
| 8 | 34: | ACATTACCCGAGACATTCCTGAC | GTTTTG | |
| 9 | 21: | TGCTGCTCCTTGTTC | GTTTTG | TCT |
| 10 | 18: | AGCTTTTGGGGACATTCTAAC | GTTTTG | TCA |
| 11 | 19: | AGATGCTTCA | GTTTTC | TCTCCGTG |
| 12 | 16: | T | CTTTTG | GACTGAAGGTTTGTTGGT |
| 13 | 12: | ATGGTC | TTTTTG | TTGTTTGTTTG |
| 14 | 9: | GTGA | CTTTTT | ACTTGTCCTAGGCTG |
| 15 | 15: | CATCTAT | GTCTTC | TTTATATTTGG |
| 16 | 14: | ACTACCTGG | TTGTGTG | CTTTCCAT |
| 17 | 25: | ATCCATGAGACTAG | GTTGGT | TAGGGTGGTG |
| 18 | 1: | CCCTCATA | GTTAA | CTTTACCTGGCTTATC |
| 19 | 10: | AGTGAACACCTTCT | GTTTCG | TGAGTC |
| 20 | 23: | CGTGT | GTCTTA | GTTAGCTCGTGG |
| 21 | 24: | TAACGTTGTGT | GTTCTG | TGCTA |
| 22 | 26: | AACAGATTTGGTCATAT | TCCTTG | G |
| 23 | 27: | TGTGTTAT | GCTCCG | GTAACAATGCCCTT |
| 24 | 30: | AATTGTA | ATTTCG | GTATCTCTG |
| 25 | 33: | GCA | ATTTCC | TGTCCAATCATGTAG |
| 26 | 36: | GCTTGAA | GCTTTC | ACCCATCCTA/GA |
| 27 | 41: | CTTCTCCTTTATAT | GTCTTA | CCA |
| 28 | 42: | TATCGAGTAGACCCTGTT | GTTCGT | G |
| 29 | 44: | CGC | GTCTAG | CTAAGATTTCTACTGATGCAT |
| 30 | 46: | ATG | ATTTTA | TGTTTATCCTGTTT |
| CLASS II | | | | |
| 3 | 45: | CAGTCGCTGTACGTGCTCTCCCTATGTAAC | | |
| 32 | 6: | CAATCGGTGTACAATATCTTCC | | |
| 33 | 28: | CGTTAGCTGGTTAGTTAGTACTAG | | |
| 34 | 3S: | AGGTAAGCGATTATGGGGTTATCG | | |
| 35 | 40: | TAGTTACATGAACTAATCGTGGAG | | |

TABLE 3

Sequences derived from the selection for the Taq polymerase

| SEQ ID NO: | CLONE NO: | SEQUENCE (5'-3') | | |
|---|---|---|---|---|
| Class I | | | | |
| 36 | 3: | TCAATACACAAATTG | ATGTACAGTG | TCGAT |

TABLE 3-continued

Sequences derived from the selection for the Taq polymerase

| SEQ ID NO: | CLONE NO: | SEQUENCE (5'-3') | | |
|---|---|---|---|---|
| 37 | 5: | CAAGCGGAAACA | ATGTACAGTA | TTGGGATC |
| 38 | 12: | G | ATGTACAGTA | TCGCTATCGAAAGAGGCTG |
| 39 | 20: | G | ATGTACAGTA | TCGCTATCGAAAGAGGCTG |
| 40 | 37: | G | ATGTACAGTA | TCGCTATCGAAAGAGGCTG |
| 41 | 38: | G | ATGTACAGTA | TCGCTATCGAAAGAGGCTG |
| 42 | 33: | GCCATTG | ATGTACAGTA | TCAATGCTGC |
| 43 | 10: | AA | GTGTACAGTA | GTTGCCTACGCTAGTG |
| 44 | 16: | AA | GTGTACAGTA | GTTGCCTACGCTAGTG |
| 45 | 27: | A | ATGTGCAGTA | TTGATATCGCTGGTGGTCA |
| 46 | 28: | ACA | ATGTGAAGTA | TTGGGGTACGTCAGTAG |
| 47 | 29: | AATTGGGAAACA | ATGTGCAGTA | TGTGAAGG |
| 48 | 6: | AA | GTGTGCAGTA | GTTACTCATAAGAGACCA |
| 49 | 15: | A | GTGTGCAGTA | GTGTGATGTCAGAGTATCC |
| 50 | 18: | A | GTGTGCGGTA | GTGTGATCTGAGAGTATCC |
| 51 | 26: | A | GTGTGTAGTA | GTGTTACGATGGGGACGG |
| 52 | 34: | AA | GTGTACAGTA | GTTGCCTACGCTAGTG |
| 53 | 40: | A | GTGTACAGTA | GTGTTCCCGGTAGAGCTAT |
| 54 | 44: | AAATGGGAAACA | ATGTGCAGTA | TTGGAAGG |
| 55 | 30: | AAGACC AGACA | ATGTACAGTA | TTGGCCTGA |
| | | Consensus A/GTGTA/GCATA | | |

Class II

| 56 | 2: | AGGTGGGACA | TTCTTTGCGTTATG | TCTCTGA |
|---|---|---|---|---|
| 57 | 39: | AGGAATCTGGGGCA | TTCTTTGCGTTTTG | CG |
| 58 | 21: | GATCATCTCAGAGCA | TTCTTAGCGTTTTG | T |
| 59 | 22: | GAGAACTCCG | TTCTTAGCGTATTG | GAGTCC |
| 60 | 31: | GATCATCTAAGAGCA | TTCTTAGCGTTTTG | G |
| 61 | 49: | GGGCTCGGAACA | TTCTTATAGCGTTTTG | TTCC |
| 62 | 43: | CAAAACGAGAGAGCT | TTCTGTGCGTTTAG | C |
| 63 | 7: | AATTGAAGTGACT | TTCTCTGCGTTTAG | TCG |
| 64 | 9: | CGATTGTTGAACA | TTCT-GACGTTTTG | T |
| 65 | 11: | AATCGATTGTTGAACA | TTCT-GACGTTTTG | T |
| 66 | 17: | AGAAGCATACGAAGACA | TTCC-AACGTTTTG | |
| 67 | 36: | AGAAGCATACGAAGACA | TTCCAA-CGTTTTG | |
| 68 | 41: | CTCAGGATAAGGTCA | TTCTAA-QGTTATG | A |
| 69 | 23: | GACCAAGCGTCAAGAT | ATTCAAACGTTTTA | |
| 70 | 25: | AGAAGCATACGAAGAC | ATTCCAACGTTTGG | |
| 71 | 42: | TACGCTGA | CAGGCCACGTTTTG | TCATGAT |
| 72 | 50: | ATAGGCAGGGGAC | ATTGCAACCTTTTG | TCA |

Class III

| 73 | 4: | CATTGGGCCAGAGGAACACAACCTCAACAG | | |
|---|---|---|---|---|
| 73 | 9: | CATTGGGCCAGAGGAACACAACCTCAACAG | | |

---

We claim:

1. A method for performing the Polymerase Chain Reaction (PCR) comprising:
   a) mixing a sample containing a nucleic acid sequence that is to be amplified with primers that are complementary to the sequences that flank the sequence to be amplified, a thermostable polymerase, and a single-stranded nucleic acid ligand to the polymerase that is capable of inhibiting said polymerase, wherein the inhibition of the polymerase by said nucleic acid is temperature dependent;
   b) heating said mixture to a temperature at which said nucleic acid ligand no longer inhibits said polymerase; and
   c) performing the standard PCR steps of melting the target nucleic acid, annealing the primers to the target nucleic acid, and synthesizing the target nucleic acid, by thermal cycling of the mixture.

2. A PCR kit comprising a thermostable DNA polymerase and a single-stranded nucleic acid ligand to said thermostable DNA polymerase that inhibits the activity of said polymerase, wherein the inhibition of said polymerase by said nucleic ligand is temperature dependent.

3. The method of claim 1 wherein said thermostable polymerase is selected from *Thermus aquaticus* (Taq polymerase) or *Thermus thermophilus* (Tth polymerase).

* * * * *